United States Patent
Schirra et al.

(10) Patent No.: US 9,730,759 B2
(45) Date of Patent: Aug. 15, 2017

(54) SPECTRAL IMAGING BASED DECISION SUPPORT, TREATMENT PLANNING AND/OR INTERVENTION GUIDANCE

(71) Applicant: KONINKLIJKE PHILIPS N.V., Eindhoven (NL)

(72) Inventors: Carsten Oliver Schirra, St. Louis, MO (US); Ewald Roessl, Henstedt-Ulzburg (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 153 days.

(21) Appl. No.: 14/402,121

(22) PCT Filed: May 31, 2013

(86) PCT No.: PCT/IB2013/054490
§ 371 (c)(1),
(2) Date: Nov. 19, 2014

(87) PCT Pub. No.: WO2013/186661
PCT Pub. Date: Dec. 19, 2013

(65) Prior Publication Data
US 2015/0110346 A1 Apr. 23, 2015

Related U.S. Application Data

(60) Provisional application No. 61/659,579, filed on Jun. 14, 2012, provisional application No. 61/722,258, filed on Nov. 5, 2012.

(51) Int. Cl.
*G06K 9/00* (2006.01)
*A61B 19/00* (2006.01)
(Continued)

(52) U.S. Cl.
CPC ............ *A61B 19/50* (2013.01); *A61B 6/032* (2013.01); *A61B 6/405* (2013.01); *A61B 6/4042* (2013.01);
(Continued)

(58) Field of Classification Search
None
See application file for complete search history.

(56) References Cited

U.S. PATENT DOCUMENTS

| 8,213,566 B2 | 7/2012 | Roessl | |
| 2004/0172303 A1* | 9/2004 | Declerck | G06F 19/3468 705/2 |

(Continued)

FOREIGN PATENT DOCUMENTS

| EP | 2433566 A2 | 3/2012 |
| WO | 2008078231 A1 | 7/2008 |

OTHER PUBLICATIONS

Youssef, et al., "Coronary artery calcium scoring, what is answered and what questions remain", Cardiovascular Diagnosis and Therapy, vol. 2, No. 2, Jun. 11, 2012, pp. 94-105.
(Continued)

*Primary Examiner* — Manuchehr Rahmjoo

(57) ABSTRACT

A method includes obtaining first spectral image data, which includes at least a first component corresponding to a targeted first K-edge based contrast agent administered to a subject if a target of the targeted first K-edge based contrast agent is present in the subject, decomposing the first spectral image data into at least the first component, reconstructing the first component thereby generating a first image of the targeted first K-edge contrast agent, determining if the targeted first K-edge contrast agent is present in the first image, and generating a signal indicating the targeted first K-edge contrast agent is present in the first image in
(Continued)

response to determining the targeted first K-edge contrast agent is present in the first image.

22 Claims, 4 Drawing Sheets

(51) Int. Cl.
      *A61B 6/03*       (2006.01)
      *A61B 6/00*       (2006.01)
      *G06T 7/00*       (2017.01)
      *G06T 11/00*       (2006.01)
      *A61B 34/10*       (2016.01)

(52) U.S. Cl.
      CPC ............ *A61B 6/4241* (2013.01); *A61B 6/481* (2013.01); *A61B 6/488* (2013.01); *A61B 6/504* (2013.01); *A61B 6/507* (2013.01); *A61B 6/5217* (2013.01); *A61B 6/5235* (2013.01); *A61B 34/10* (2016.02); *G06T 7/0012* (2013.01); *G06T 11/005* (2013.01); *A61B 2034/107* (2016.02); *F04C 2270/041* (2013.01); *G06T 2207/10081* (2013.01); *G06T 2207/30101* (2013.01); *G06T 2211/404* (2013.01)

(56) References Cited

U.S. PATENT DOCUMENTS

| | | | |
|---|---|---|---|
| 2008/0167552 A1* | 7/2008 | Bouchevreau | A61B 6/481 600/431 |
| 2010/0008558 A1* | 1/2010 | Baeumer | A61B 6/405 382/131 |
| 2010/0069742 A1* | 3/2010 | Partain | A61N 5/1049 600/424 |
| 2010/0104161 A1* | 4/2010 | Ziegler | G06T 11/005 382/131 |
| 2010/0111388 A1* | 5/2010 | Seppi | A61B 6/032 382/130 |
| 2010/0208962 A1* | 8/2010 | Roessl | G06T 11/005 382/131 |
| 2011/0103550 A1 | 5/2011 | Proksa | |
| 2011/0123082 A1* | 5/2011 | Proksa | G06T 11/006 382/131 |
| 2011/0182492 A1* | 7/2011 | Grass | A61B 6/4441 382/131 |
| 2013/0308847 A1 | 11/2013 | Schirra et al. | |

OTHER PUBLICATIONS

Baturin, P., et al.; Spectral CT imaging of vulnerable plaque with two independent biomarkers; 2012; Phys. Med. Biol.; 57:4117-4138.

Cormode, D. P., et al.; Atherosclerotic Plaque Composition: Analysis with Multicolor CT and Targeted Gold Nanoparticles; 2010; Radiology; 256(3)774-782.

Korosoglou, G., et al.; Assessment of atherosclerotic plaque composition using 256-slice CT and association with biochemical markers; 2011; MedicaMundi; 55(1)7 pages.

Meyer, C. H.; Novel Atherosclerotic Plaque Detection/Assessment Technique for the Treatment of Heart Disease; 2012; Uvainnovates; http://uva.technologypublisher.com/technology/9068.

Pan, D., et al.; Computed Tomography in Color: NanoK-enhanced Spectral CT Molecular Imaging; 2010; Angew. Chem. Int. ;49(50)9635-9639.

Roessl, E., et al.; K-edge imaging in x-ray computed tomography using multi-bin photon counting detectors; 2007; Phys. Med. Biol.; 52:4679-4696.

Roessl, E., et al.; Preclinical spectral computed tomography of gold nano-particles; 2011; Nuclear Instruments and Methods in Physics Research A; 648:S259-S264.

Schultke, E., et al.; Synchrotron-based intra-venous K-edge digital subtraction angiography in a pig model: A feasibility study; 2010; European Journal of Radiology; 73:677-681.

\* cited by examiner

SPECTRAL IMAGING BASED DECISION SUPPORT, TREATMENT PLANNING AND/OR INTERVENTION GUIDANCE

CROSS REFERENCE TO RELATED APPLICATIONS

This application is a national filing of PCT application Serial No. PCT/IB2013/054490, filed May 31, 2013, published as WO 2013/186661 A1 on Dec. 19, 2013, which claims the benefit of U.S. provisional application Ser. No. 61/659,579 filed Jun. 14, 2012 and U.S. provisional application Ser. No. 61/722,258 filed Nov. 5, 2012, both of which are incorporated herein by reference.

The following generally relates to spectral imaging based decision support, treatment planning and/or intervention guidance and is described with particular application to computed tomography (CT); however, the following is also amenable to other imaging modalities.

A person experiencing chest pain often ends up in the emergency room (ER). Generally, chest pain may be a symptom of a number of conditions, including cardiac and non-cardiac in origin. Such a person may have no history of cardiac disease, and the origin of the chest pain may be unknown. A typical approach to diagnosing the person is to rule out certain causes of chest pain (differential diagnosis) such as myocardial infarction (MI or heart attack), pulmonary embolism, thoracic aortic dissection, etc. A standard procedure of the ER is to test troponin (a protein of muscles) levels and perform an electrocardiogram (ECG) to obtain signals representative of the electrical activity of the heart.

The ER physician ends up having to decide between admitting the person for observation and testing or discharging the person with further outpatient management. Incorrectly discharging a person with acute coronary syndrome (ACS) may lead to death. As a result, the decision pendulum typically is biased toward hospital admission, which exposes the person pathogens of other patients and results in healthcare costs. Patients admitted for ACS typically undergo cardiac telemetry, several ECGs, repeated cardiac troponin assays over 12 to 24 hours, which if negative, are followed up with non-invasive cardiac stress testing. Unfortunately, such testing is performed over several hours which delays the decision, inconveniences the person, and has resulted in overnight hospitalization.

A conventional CT scanner generally includes an x-ray tube mounted on a rotatable gantry opposite a detector array across an examination region. The rotatable gantry, and hence the x-ray tube, can be rotated, under system control, around the examination region. The rotatable gantry, and hence the x-ray tube, can also be parked or held at a static angular position with respect to the examination region. The x-ray tube is configured to emit radiation that traverses the examination region and is detected by the detector array. The detector array, in response, generates and outputs a signal indicative of the detected radiation. The signal is reconstructed to generate volumetric image data.

The image data includes voxels that are represented in terms of gray scale values corresponding to relative radiodensity that reflect attenuation characteristics of the scanned subject and generally show structure such as anatomical structures within the scanned subject. Since the absorption of a photon by a material is dependent on the energy of the photon traversing the material, the detected radiation also includes spectral information, which provides additional information indicative of the elemental or material composition (e.g., atomic number) of the scanned material of the subject. Unfortunately, conventional CT data does not reflect the spectral characteristics as the signal output by the detector array is proportional to the energy fluence integrated over the energy spectrum.

A spectral CT scanner captures the above-noted spectral characteristics. Generally, a spectral CT scanner may include two or more x-ray tubes that emit radiation with different mean spectrums, one x-ray tube that is switched between different emission voltages, and/or an x-ray tube and an energy-resolving detector (e.g., photon counting, at least two photodiodes with different spectral sensitivities, etc.) and discrimination electronics. K-edge spectral imaging leverages the phenomena that high-Z elements tend to attenuate photons to a much higher extent above a particular energy (the K-edge energy of the given element) relative to attenuating photons just below the K-edge energy. The discontinuity in the attenuation behavior can be detected using an energy-resolving detector.

Patent application Ser. No. 61/479,866, filed on Apr. 28, 2011, entitled "SPECTRAL IMAGING," and assigned to Koninklijke Philips Electronics N.V., which is incorporated by reference herein in its entirety, describes an approach in which spectral CT and K-edge imaging is used to evaluate vulnerable plaque via pre-scan 2D projection images and/or volumetric image data to differentiate patients with ACS in the ER from other causes of chest pain and provide screening to either discharge a person or admit the person for an interventional procedure. Fluoroscopy has been utilized during the interventional procedure to guide the interventional procedure, which exposes the person to further radiation, which may increase risk of cancer. Thus, there is an unresolved need to leverage the pre-interventional procedure image data to facilitate the interventional procedure and/or reduce patient dose.

Aspects described herein address the above-referenced problems and others.

In one aspect, a method includes obtaining first spectral image data, which includes at least a first component corresponding to a targeted first K-edge based contrast agent administered to a subject if a target of the targeted first K-edge based contrast agent is present in the subject, decomposing the first spectral image data into at least the first component, reconstructing the first component thereby generating a first image of the targeted first K-edge contrast agent, determining if the targeted first K-edge contrast agent is present in the first image, and generating a signal indicating the targeted first K-edge contrast agent is present in the first image in response to determining the targeted first K-edge contrast agent is present in the first image.

In another aspect, a processing apparatus includes a signal decomposer that decomposes first spectral image data into at least a first component, wherein the first spectral image data includes the at least first component, which corresponds to a targeted first K-edge based contrast agent administered to a subject, if a target of the targeted first K-edge based contrast agent is present in the subject. The processing apparatus further includes a first K-edge component reconstructor that reconstructs the first component thereby generating a first image of the targeted first K-edge contrast agent. The processing apparatus further includes a decision support system that evaluates the first image and determines if the targeted first K-edge contrast agent is present in the first image and generates a signal indicating the targeted first K-edge contrast agent is present in the first image in response to determining the targeted first K-edge contrast agent is present in the first image.

In another aspect, a method includes performing a spectral scan of a subject in which a single scan images at least two different K-edge contrast agents administered to a subject, including a targeted first K-edge contrast agent with an affinity to vessel plaque and a second blood pool K-edge contrast agent, generating spectral image data, decomposing the spectral image data into at least two components, including a first component corresponding to the first targeted first K-edge contrast agent and a second component corresponding to second blood pool K-edge contrast agent, generating a first spectral image of the vessel plaque based on the first component and an angiogram based on the second component, and generating an intervention procedure plan based at least on the first image and the angiogram.

The invention may take form in various components and arrangements of components, and in various steps and arrangements of steps. The drawings are only for purposes of illustrating the preferred embodiments and are not to be construed as limiting the invention.

FIG. 1 schematically illustrates a spectral imaging apparatus in connection with an imaging data processing apparatus that generates data that facilitates an interventional procedure.

The following describes a spectral imaging approach in which a targeted first K-edge contrast agent, targeted to plaque in a vessel, is employed to generate a first K-edge image corresponding to the plaque (or a plaque image) that is used to facilitate determining whether plaque is present in the vessel and, if so, whether an interventional procedure is to be performed to treat the plaque. If it is determined that an interventional procedure is to be performed, both the plaque image and a blood pool image are used to plan the interventional procedure, and the interventional procedure plan and one or both of the images are used to perform and guide the interventional procedure.

As described in greater detail below, in one instance, image data from a single scan includes components corresponding to the first contrast agent and a second blood pool contrast agent (used to generate the blood pool image), which are both K-edge based contrast agents. This allows for reducing dose and scan time relative to performing two separate scans. Also described in greater detail below, in another instance, separate scans are performed, wherein the second blood pool contrast agent is only administered if plaque is found and an intervention ordered. This allows for reducing contrast agent exposure unless plaque is found. In this instance, the second blood pool contrast agent may be a K-edge based contrast agent or a conventional (non-spectral) based contrast agent.

Figure 1:
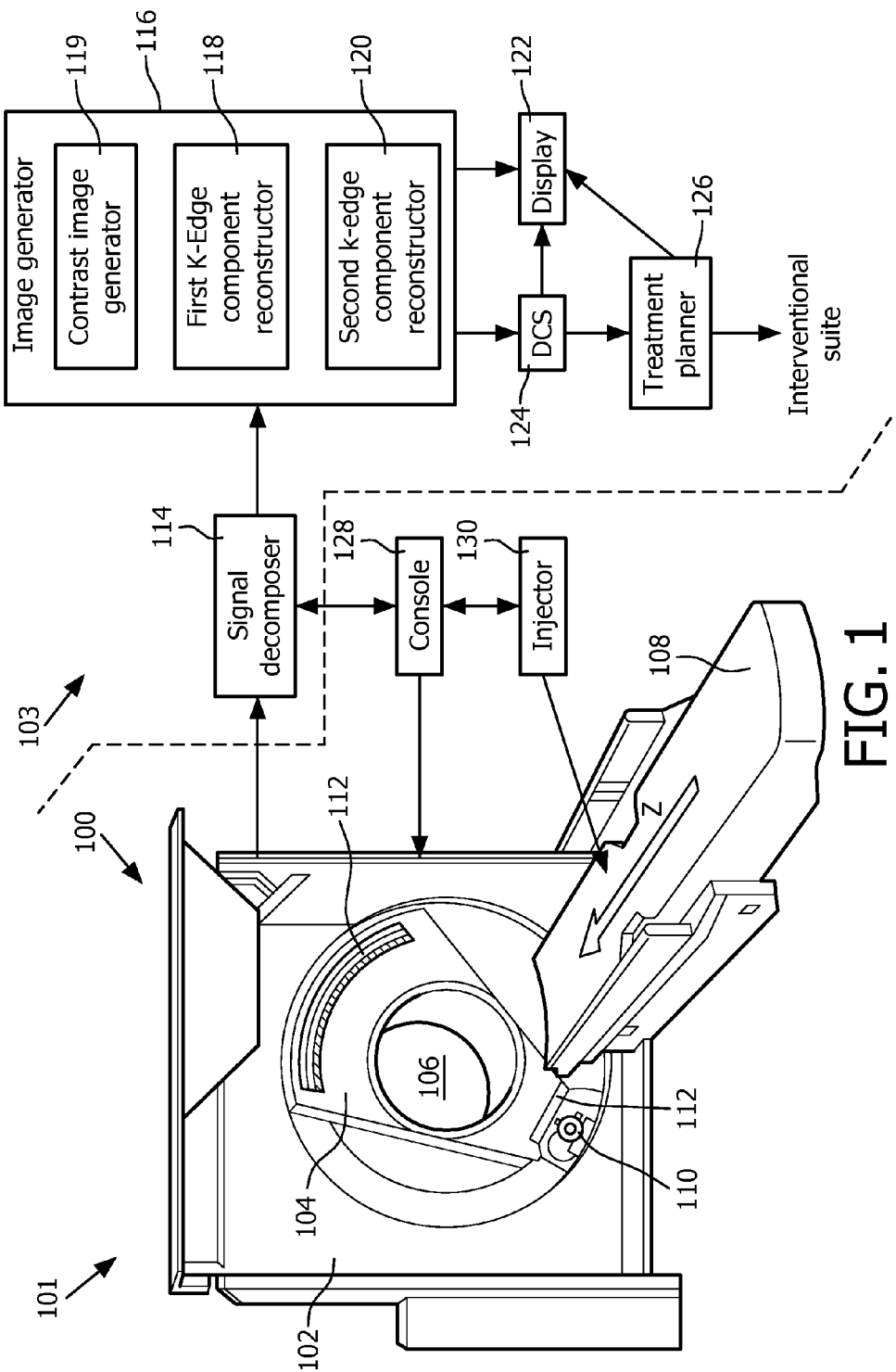

Turning to FIG. 1, a system 101 includes an imaging apparatus 100 and an imaging data processing apparatus 103 that process signals generated by the imaging apparatus 100 and/or other imaging apparatus. In another embodiment, at least one of the components of the imaging data processing apparatus 103 can be part of the imaging apparatus 100.

The illustrated imaging apparatus 100 includes a computed tomography (CT) scanner. The imaging apparatus 100 includes a generally stationary gantry 102 and a rotating gantry 104, which is rotatably supported by the stationary gantry 102. The rotating gantry 104 rotates around an examination region 106 about a longitudinal or z-axis. A subject support 108 such as a couch supports a human or animal patient or an object in the examination region 106. The subject support 108 is movable in coordination with scanning so as to guide the subject or object with respect to the examination region 106 before, during and/or after scanning.

A radiation source 110, such as an x-ray tube, is supported by the rotating gantry 104 and emits poly-energetic/chromatic radiation that traverses the examination region 106. A radiation sensitive detector array 112 is located opposite the radiation source 110 across the examination region 106 and detects radiation traversing the examination region 106. The illustrated radiation sensitive detector array 112 includes an energy-resolving detector such as a direct conversion detector and/or a scintillator/photodiode based multi-spectral detector. The radiation sensitive detector array 112 may include one or multiple rows of detectors arrange with respect to each other along the z-axis. The radiation sensitive detector array 112 generates and outputs a signal indicative thereof.

A signal decomposer 114 decomposes the signal into energy-dependent components. For example, the signal can be decomposed into a Compton component, a photo-electric component, and one or more K-edge components representative of one or more K-edge materials of one or more administered contrast agents. In one instance, a first K-edge contrast agent is a targeted contrast agent with an affinity for vessel plaque, while a second K-edge contrast agent is a blood pool contrast agent. Where the contrast agents are administered for a single scan, the K-edge energies are separated by a suitable amount (e.g., 5 or more keV) to mitigate, e.g., the first K-edge contrast agent circulating through the circulatory system and being mistaken as the second K-edge contrast agent.

Suitable signal decomposition algorithms include a maximum likelihood signal decomposition algorithm and/or other signal decomposition algorithms. An example of a suitable signal decomposition approach is described in international application serial number PCT/IB2007/055105, filed on Dec. 14, 2007, published as WO2008/078231A1 and assigned to Koninklijke Philips Electronics N.V., which is incorporated in their entirety herein by reference. Another example of a suitable signal decomposition approach is described in "K-edge imaging in x-ray computed tomography using multi-bin photon counting detectors," E. Roessl and R. Proksa, 2007 Phys. Med. Biol. 52 4679-4696. Other signal decomposition approaches are also contemplated herein.

An image generator 116 processes the signal and/or one or more of the decomposed components and generates one or more images indicative thereof. In the illustrated embodiment, the image generator 116 includes a first K-edge component reconstructor 118 that processes the decomposed component corresponding to a first K-edge energy and generates a first image, and a second K-edge component reconstructor 120 that processes the decomposed component corresponding to a second different K-edge energy and generates a second image. Although shown as two separate reconstructors, the reconstructor 118 and 120 can be the same reconstructor.

A decision support system (DCS) 124 evaluates the image(s) generated by the image generator 116 and generates a signal indicative of an evaluation result. By way of example, where the targeted first K-edge contrast agent targets vessel plaque, the DCS 124 can evaluate the first image and determine whether the image includes voxels with values representing vessel plaque. Where the voxels indicate a presence of vessel plaque, the DCS 124 can generate a signal indicating a presence of vessel plaque, a quantity of vessel plaque via the amount of contrast agent, a location of the vessel plaque, a recommended course of action, etc.

An example of a recommended course of action is to acquire an angiogram, e.g., for a scan of the subject where only a vessel plaque targeted K-edge contrast agent was administered for the scan and a blood pool contras agent was not administered for the scan. In this case, a second scan with the blood pool K-edge contrast agent can be performed with the imaging apparatus 100. Another example of a recommended course of action is to generate an interventional procedure plan and perform an interventional procedure based thereon. The particular recommended course of action can be based on a set of predetermined rules or otherwise.

A treatment planner 126 facilitates generating an interventional treatment plan, automatically and/or manually with user interaction. In the illustrated embodiment, the treatment planner 126 does this in response to the DCS 124 recommending generation of an interventional plan and/or an input indicative of a user employing the treatment planner 126, based on the vessel plaque image, the blood pool image, and/or other data. The treatment planner 126 visually presents the treatment plan and can forward the treatment plan to another computing system such as a computing system located in an interventional suite in which the intervention is to be performed.

The image generator 116, the DCS 124, and/or the treatment planner 126 may support known and/or other image processing tools such as zoom, pan, segment, etc. and can present, via a display 122, individual images, combined images, manipulate images, etc. For example, the display 122 can visually display one or more structural images, one or more contrast images, a quantified contrast material level (e.g., numerically and/or through color coding, highlighting, etc.), a recommended course of action, an interventional treatment plane, etc. Such data can be displayed based on default settings, user preferences, etc. The data can also be conveyed to a PACS, RIS, HIS, and/or other storage system.

A general purpose computer serves as an operator console 128. The console 128 includes a human readable output device such as a monitor or display and an input device such as a keyboard and mouse. Software resident on the console 128 allows the operator to interact with the scanner 100 via a graphical user interface (GUI) or otherwise. This interaction may include selecting a scan protocol such as a vessel plaque, a blood pool, and/or other K-edge imaging or non K-edge scan protocol, initiating scanning, etc.

An injector 130 is configured to inject a contrast agent such as a K-edge vessel plaque targeted contrast agent, a K-edge vessel blood pool agent, a conventional (non-spectral) contrast agent, and/or other contrast agent. The illustrated injector 130 is controlled by the console 128, which triggers or invokes in the injector 130 to administer the contrast material in coordination with invoking scanning such that peak contrast uptake and enhancement by tissue of interest is scanned during a single respiratory cycle. The contrast agent(s) can additionally or alternatively be manually administered by a clinician or the like. Where the contrast agent is manually administered, the injector 130 can be omitted.

A suitable targeted (e.g., tissue specific) contrast agent includes specific nano-particles, which have an affinity to the particular target (e.g., fibron of vessel plaque), and a K-edge material having a known K-edge energy. Such nano-particles can be based on elements such as bismuth, gold, gadolinium, and/or other elements with K-edge values within the diagnostic x-ray energy bandwidth (e.g., 20-140 keV). An example application of spectral CT using a suitable contrast material is discussed in "Computed Tomography in Color: NanoK-Enhanced Spectral CT Molecular Imaging," Pan, et al., 2010 Angew. Chem. Int. Ed. 49, 9635-9639.

Variations are discussed next.

In a variation, one or both of the vessel plaque and the blood pool images can be generated using a different imaging apparatus. For example, the blood pool scan can be performed with another spectral CT scanner, etc.

In another variation, the blood pool image is obtained using a conventional subtraction angiography algorithm (or alternatively by thresholding), e.g., by determining a difference image between a reference image (a non-contrast image) and an image acquired with a conventional (or non-spectral) imaging apparatus, thereby generating a contrast image. The reference image can be any image acquired without the blood pool contrast such as the vessel plaque image and/or other image. In this variation, the image generator 116 includes an optional image subtraction component 119 (FIG. 1) that performs the subtraction and produces the contrast image.

In another variation, the imaging apparatus 100 includes two or more radiation sources 102, arranged at different angular locations with respect to each other in the x/y plane, where at least two of the radiation sources 102 emit radiation with different energy spectra. At least two of the two or more radiation sources 102 can be concurrently or individually employed during a same scan and are configured to emit similar or different mean emission spectrums.

In another variation, the radiation source 102 is configured to switch between two or more emission voltages, for example, between at least two different emission voltages in a range from 10 kVp to 160 kVp. A source controller or the like can switch the radiation source voltage from scan to scan, between integration periods of a scan, within an integration period, and/or otherwise. As a result, radiation beams having different mean emission energy spectra can be generated and used to scan an object or subject.

Figure 2:
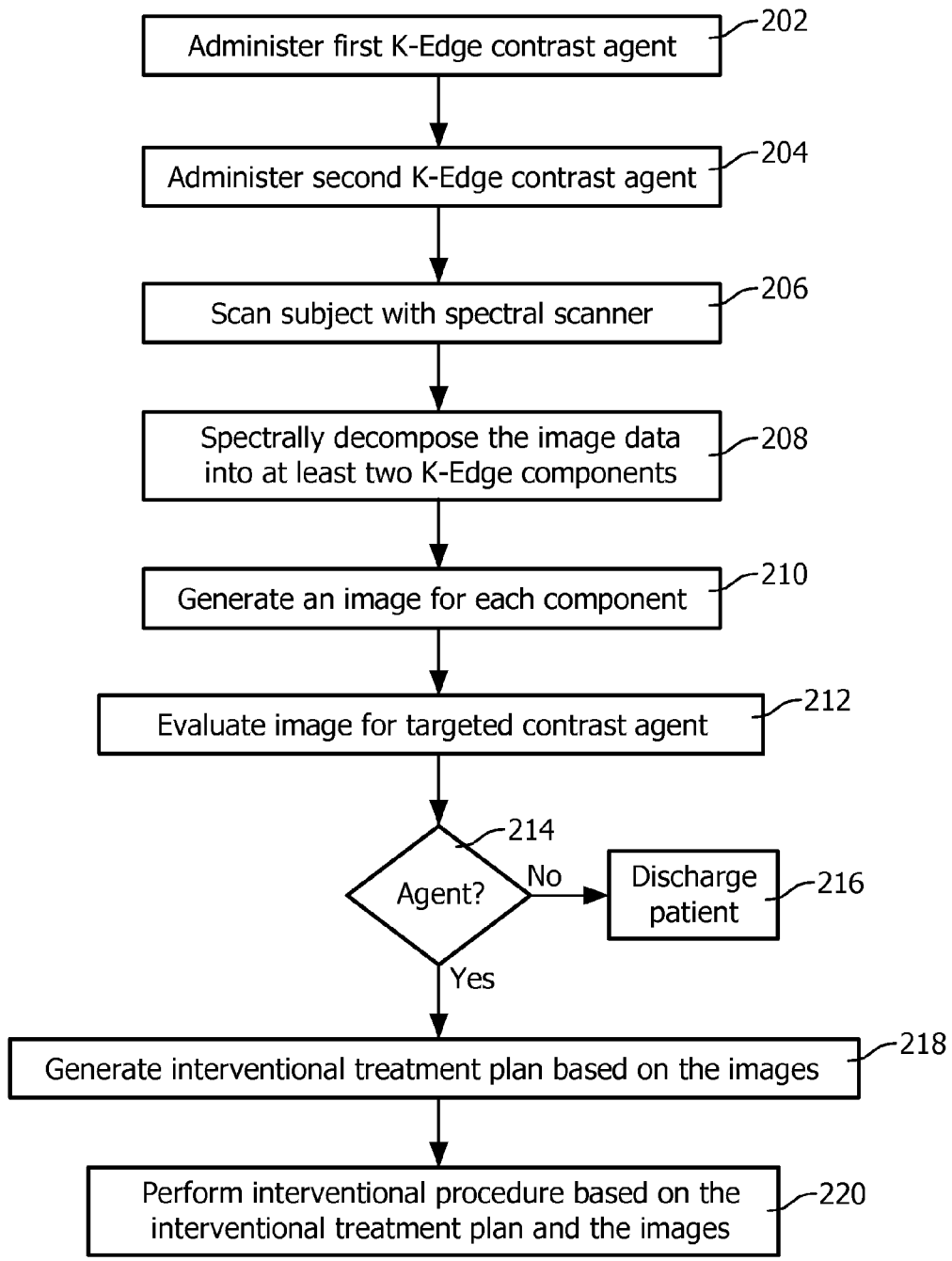
FIG. 2 illustrates an example method for facilitating an interventional procedure in which a single scan is used to acquire image data which includes components corresponding to a targeted K-edge contrast agent and a blood pool K-edge contrast agent.
Figure 3:
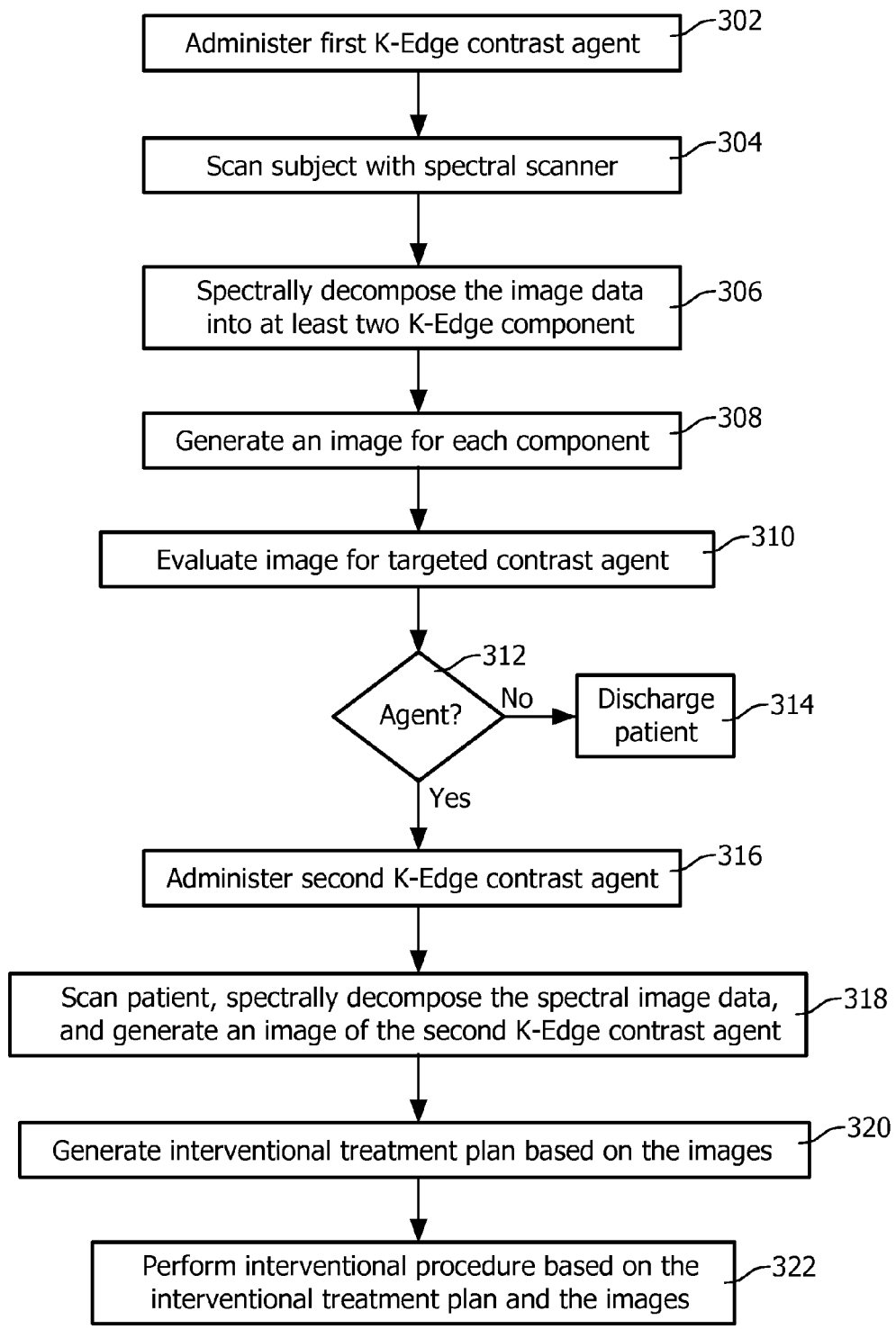
FIG. 3 illustrates an example method for facilitating an interventional procedure in which two different scans are used to acquire image data for the targeted K-edge contrast agent and the blood pool K-edge contrast agent.
Figure 4:
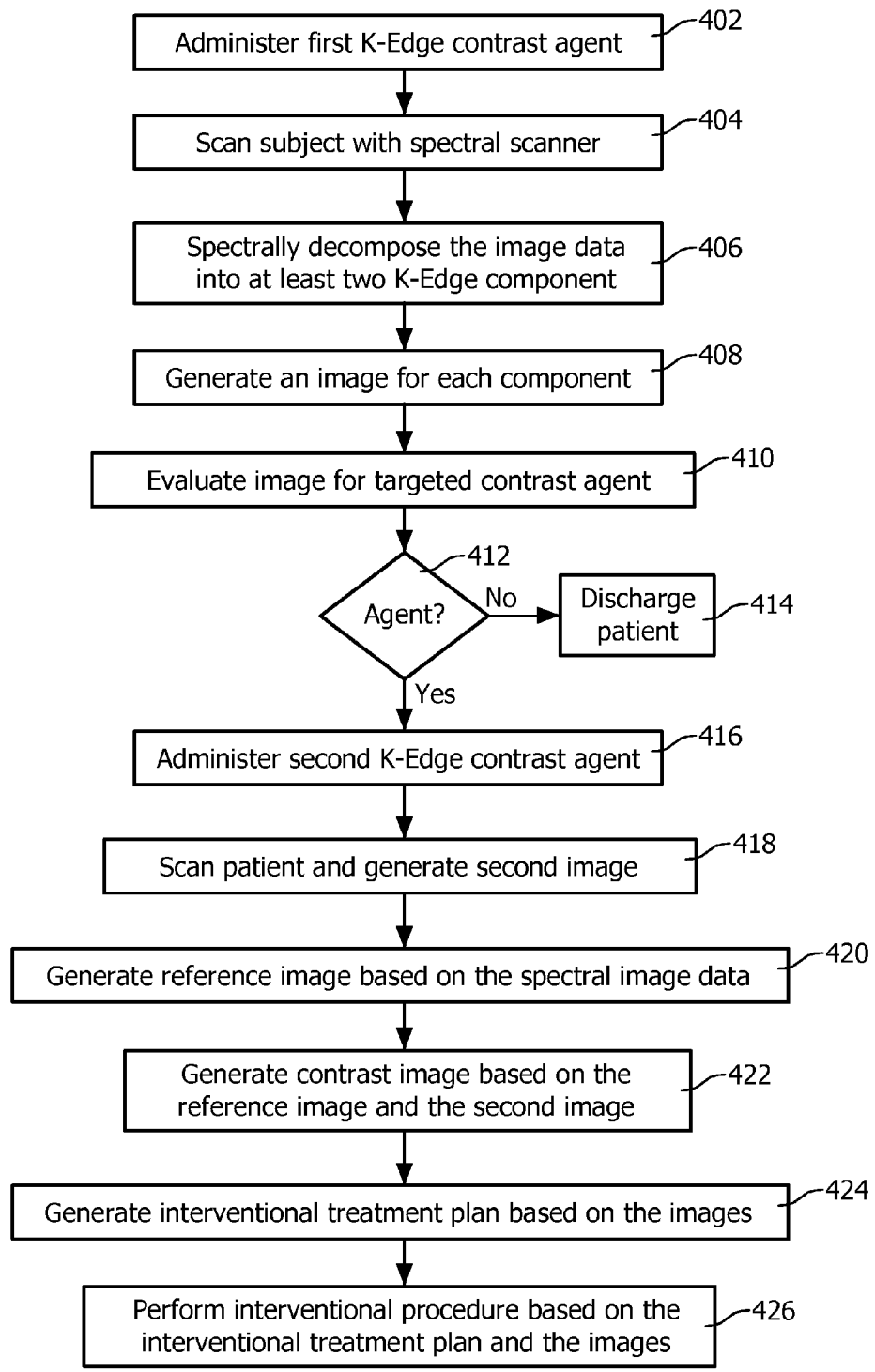
FIG. 4 illustrates an example method in which two different scans are used to acquire image data for the targeted K-edge contrast agent and a conventional (non-spectral) blood pool contrast agent.

FIGS. 2, 3, and 4 illustrate methods for employing image data to facilitate determining whether an interventional procedure should be performed, planning the interventional procedure, and/or guiding the interventional procedure.

It is to be appreciated that the ordering of the below acts is for explanatory purposes and not limiting. As such, other orderings are also contemplated herein. In addition, one or more of the acts may be omitted and/or one or more other acts may be included.

FIG. 2 illustrates an example method in which a single scan is used to acquire image data with components corresponding to a targeted K-edge contrast agent and a blood pool K-edge contrast agent.

At 202, a first K-edge contrast agent is administered to a subject. As discussed herein, the first K-edge contrast agent can be a targeted contrast agent that includes a K-edge material having a first K-edge energy and that is targeted to a structure of interest such a plaque in a vessel.

At 204, a second K-edge contrast agent is administered to the subject. As discussed herein, the second K-edge contrast agent can be a blood pool contrast agent including a K-edge material having a second K-edge energy, which is different from the first K-edge energy.

Acts 202 and 204 can occur serially (202 then 204, or 204 then 202) or concurrently.

At 206, the subject is scanned using a spectral imaging apparatus, producing spectral image data.

At 208, the image data is spectrally decomposed into at least two components, a first component corresponding to the first K-edge energy and a second component corresponding to the second K-edge energy.

At 210, a first image is generated based on the first component and a second image is generated based on the second component.

At 212, the first image is evaluated for a presence of the targeted contrast agent and hence the structure of interest.

At 214, if the targeted contrast agent is not present, then at 216 the patient is discharged.

At 214, if the targeted contrast agent is present, then at 218 the first and the second images are used to generate an interventional treatment plan for the patient.

At 220, an interventional procedure is performed based on the interventional treatment plan using at least the second image as a guide.

A non-limiting application includes identifying ruptured plaque in a vessel and planning and guiding cardiac catheterization for treatment of the ruptured plaque. In this instance, the first K-edge material is for identifying ruptured plaque and the second K-edge material is for producing an angiogram, which provides information about vessel anatomy. Generally, this method is a dual K-edge imaging approach in which a single scan acquires image data for generating both a ruptured plaque image and an angiogram.

A single scan using two separate and concurrently administered K-edge contrast agents allows for reducing dose and scan time relative to performing two separate scans, one for each K-edge contrast agent. Radiation dose can be further reduced by using the resulting images (the vulnerable plaque image and/or the angiogram) to guide the catheterization instead of the conventional approach of using fluoroscopy during execution of the interventional procedure.

Turning to FIG. 3, an example method in which two different scans are used to acquire image data for the targeted K-edge contrast agent and the blood pool K-edge contrast agent is illustrated.

At 302, a first K-edge contrast agent is administered to a patient. As discussed herein, the first K-edge contrast agent is a targeted contrast agent that includes a first K-edge material having a first K-edge energy and that is targeted to a structure of interest such as vessel plaque.

At 304, the patient is scanned using a spectral imaging apparatus, producing first spectral image data.

At 306, the spectral image data is spectrally decomposed into at least a first component corresponding to the first K-edge energy.

At 308, a first image is generated based on the first component.

At 310, the first image is evaluated for a presence of the targeted contrast agent and hence the structure of interest.

At 312, if the targeted contrast agent is not present, then at 314 the patient is discharged.

At 312, if the targeted contrast agent is present, then at 316 a second K-edge contrast agent is administered to the subject. As discussed herein, the second K-edge contrast agent is a blood pool contrast agent including a second K-edge material having a second K-edge energy.

At 318, the patient is scanned using the same or a different spectral imaging apparatus, producing second spectral image data, which is spectrally decomposed into at least a second component corresponding to the second K-edge energy, and a second image is generated base thereon.

At 320, the first and the second images are used to generate an interventional treatment plan for the patient.

At 322, an interventional procedure is performed based on the interventional treatment plan using at least the second image as a guide.

Again, a non-limiting application includes identifying ruptured plaque in a vessel and planning and guiding catheterization for treatment of the plaque. Likewise, the first K-edge material is for identifying ruptured plaque and the second K-edge material is for producing an angiogram. In this instance, the K-edge contrast agents are administered for separate scans. The first K-edge contrast agent is used to identify ruptured plaque.

Only if ruptured plaque is identified and a catheterization ordered is the K-edge blood pool contrast agent administered and a second spectral CT scan performed to produce the angiogram. This approach avoids administration of the K-edge blood pool contrast agent unless vulnerable plaque is identified and a catheterization ordered, reducing exposure to the contrast agent unless a catheterization is ordered, with the trade-off being additional dose from the second scan.

Next at FIG. 4, an example method in which two different scans are used to acquire image data for the targeted K-edge contrast agent and a conventional (non-spectral) blood pool contrast agent is illustrated.

At 402, a first K-edge contrast agent is administered to a patient. As discussed herein, the first K-edge contrast agent is a targeted contrast agent that includes a first K-edge material having a first K-edge energy and that is targeted to a structure of interest such as vessel plaque.

At 404, the patient is scanned using a spectral imaging apparatus, producing spectral image data.

At 406, the spectral image data is spectrally decomposed into at least a first component corresponding to the first K-edge energy.

At 408, a first image is generated based on the first component.

At 410, the first image is evaluated for a presence of the targeted contrast agent and hence the structure of interest.

At 412, if the targeted contrast agent is not present, then at 414 the patient is discharged.

At 412, if the targeted contrast agent is present, then at 416 a reference image is generated based on the spectral image data. The image is a reference image for detecting a presence of the second contrast agent since the spectral image data is acquired without administration of the second blood pool contrast agent.

At 418, a second contrast agent is administered to the subject. As discussed herein, the second contrast agent is a blood pool contrast agent.

At 420, the patient is scanned using a non-spectral imaging apparatus, producing second image data, and a second image is generated based on the second image data.

At 422, a contrast image is generated based on a difference between the reference image and the second image.

At 424, the first image and the contrast image are used to generate an interventional treatment plan for the patient.

At 426, an interventional procedure is performed based on the interventional treatment plan using at least the contrast image as a guide.

Again, a non-limiting application includes identifying vulnerable plaque in a vessel and planning and guiding catheterization for treatment of the vulnerable plaque. Likewise, the first K-edge material is for identifying vulnerable plaque and the second K-edge material is for producing an angiogram. Similar to FIG. 3, the K-edge contrast agents are administered for separate scans. The first K-edge contrast agent is again used to identify vulnerable plaque.

Only if vulnerable plaque is identified and a catheterization ordered is the non-spectral blood pool contrast agent administered and a second CT scan performed to produce the angiogram. This approach avoids administration of the non-spectral blood pool contrast agent unless vulnerable plaque is identified and a catheterization ordered, reducing exposure to the contrast agent unless a catheterization is ordered, with the trade-off being additional dose from the second scan and moving the patient from a spectral scanner to a non-spectral scanner.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention claimed is:

1. A method, comprising:
    obtaining first spectral image data, which includes at least a first component corresponding to a targeted first K-edge based contrast agent administered to a subject if a target of the targeted first K-edge based contrast agent is present in the subject;
    decomposing the first spectral image data into at least the first component;
    reconstructing the first component thereby generating a first image of the targeted first K-edge contrast agent;
    determining if the targeted first K-edge contrast agent is present in the first image;
    generating a signal indicating the targeted first K-edge contrast agent is present in the first image in response to determining the targeted first K-edge contrast agent is present in the first image;
    obtaining second spectral image data, which includes a second component corresponding to a second K-edge based contrast agent administered to the subject;
    decomposing the second spectral image data into at least the second component; and
    reconstructing the second component thereby generating a second image of the second K-edge contrast agent.

2. The method of claim 1, wherein the first spectral image data and the second spectral image data are respectively from first and second different spectral scans of the subject.

3. The method of claim 2, wherein the second spectral scan is performed only in response to generating the signal indicating the targeted first K-edge contrast agent is present in the first image.

4. The method of claim 1, further comprising:
    generating an intervention treatment plan based on the first and second images.

5. The method of claim 1, wherein the second contrast agent is a blood pool contrast agent.

6. The method of claim 1, wherein the targeted first K-edge based contrast agent has an affinity to vessel plaque.

7. A method, further comprising:
    obtaining first spectral image data, which includes at least a first component corresponding to a targeted first K-edge based contrast agent administered to a subject if a target of the targeted first K-edge based contrast agent is present in the subject;
    decomposing the first spectral image data into at least the first component;
    reconstructing the first component thereby generating a first image of the targeted first K-edge contrast agent;
    determining if the targeted first K-edge contrast agent is present in the first image;
    generating a signal indicating the targeted first K-edge contrast agent is present in the first image in response to determining the targeted first K-edge contrast agent is present in the first image
    obtaining a second image data, which includes a second component corresponding to a second non-spectral based contrast agent administered to the subject;
    reconstructing the second non-spectral image data thereby generating a second image of the second non-spectral based contrast agent;
    reconstructing the first spectral image data thereby generating a reference image without the second non-spectral based contrast agent; and
    generating a contrast image based on a difference between the second image and the reference image.

8. The method of claim 7, wherein the first spectral image data and the second image data are respectively from a first spectral scan and a second non-spectral spectral scan of the subject respectively by a spectral imaging apparatus and a non-spectral imaging apparatus.

9. The method of claim 8, wherein the second non-spectral spectral scan is performed only in response to generating the signal indicating the targeted first K-edge contrast agent is present in the first image.

10. The method of claim 8, further comprising:
    generating an intervention treatment plan based on the first image and the contrast image.

11. The method of claim 7, further comprising:
    employing the intervention treatment plan during execution of a corresponding treatment procedure.

12. The method of claim 11, further comprising:
    using at least one of the images to guide the intervention treatment procedure.

13. A processing apparatus, comprising:
    one or more processors that:
        decomposes first spectral image data into at least a first component,
        wherein the first spectral image data includes the at least first component, which corresponds to a targeted first K-edge based contrast agent administered to a subject, if a target of the targeted first K-edge based contrast agent is present in the subject;
        reconstructs the first component thereby generating a first image of the targeted first K-edge contrast agent;
        evaluates the first image and determines if the targeted first K-edge contrast agent is present in the first image and generates a signal indicating the targeted first K-edge contrast agent is present in the first image in response to determining the targeted first K-edge contrast agent is present in the first image; and determines a contrast image based on a difference between an image of a second non-spectral contrast agent generated from non-spectral scan acquired with a non-spectral imaging apparatus and an image generated from the first spectral image data.

14. The processing apparatus of claim 13, wherein the first spectral image data includes a second component corresponding to a second K-edge based contrast agent administered to the subject and the one or more processors decomposes the spectral image data into the second component, and reconstructs the second component thereby generating a second image of the second K-edge contrast agent, wherein the first spectral image data is generated from a single spectral scan in which both the targeted first and the second K-edge contrast agents are present in the subject.

15. The processing apparatus of claim 14, wherein the one or more processors generates an intervention treatment plan based on the first and second images.

16. The processing apparatus of claim 15, further comprising:

employing the intervention treatment plan during execution of a corresponding treatment procedure.

17. The processing apparatus of claim 16, further comprising:

using at least one of the images to guide the intervention treatment procedure.

18. The processing apparatus of claim 14, wherein the second contrast agent is a blood pool contrast agent.

19. The processing apparatus of claim 13, wherein the one or more processor decomposes second spectral image data, which includes a second component corresponding to a second based contrast agent administered to the subject, generating at least the second component; and reconstructs the second component thereby generating a second K-edge image of the second K-edge contrast agent, wherein the first spectral image data and the second spectral image data are respectively from first and second different spectral scans of the subject, and the second spectral scan is performed only in response to generating the signal indicating the targeted first K-edge contrast agent is present in the first image.

20. The processing apparatus of claim 13, wherein the non-spectral scan is performed only in response to generating the signal indicating the targeted first K-edge contrast agent is present in the first image.

21. The processing apparatus of claim 13, wherein the one or more processors generates an intervention treatment plan based on the first image and the contrast image.

22. The processing apparatus of claim 13, wherein the targeted first K-edge based contrast agent has an affinity to vessel plaque.

* * * * *